US010139121B2

United States Patent
Jung et al.

(10) Patent No.: US 10,139,121 B2
(45) Date of Patent: Nov. 27, 2018

(54) AIR CONDITIONER

(71) Applicant: Samsung Electronics Co., Ltd., Suwon-si (KR)

(72) Inventors: Jae Rim Jung, Asan-si (KR); Se Kwan Jeong, Osan-si (KR); Jong Whal Kim, Suwon-si (KR); Tae Duk Kim, Yongin-si (KR); Yun Suk Park, Suwon-si (KR); Sun-Hee Son, Suwon-si (KR); Young Seok Lim, Suwon-si (KR); Hee-Soo Jung, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 200 days.

(21) Appl. No.: 14/951,812

(22) Filed: Nov. 25, 2015

(65) Prior Publication Data

US 2016/0238509 A1 Aug. 18, 2016

(30) Foreign Application Priority Data

Feb. 17, 2015 (KR) .................. 10-2015-0024055

(51) Int. Cl.
| | |
|---|---|
| *F24F 11/00* | (2018.01) |
| *G01N 15/02* | (2006.01) |
| *F24F 11/30* | (2018.01) |
| *G01N 15/00* | (2006.01) |
| *F24F 13/20* | (2006.01) |
| *F24F 110/50* | (2018.01) |
| *F24F 110/64* | (2018.01) |

(52) U.S. Cl.
CPC .......... *F24F 11/0017* (2013.01); *F24F 11/30* (2018.01); *G01N 15/02* (2013.01); *F24F 13/20* (2013.01); *F24F 2110/50* (2018.01); *F24F 2110/64* (2018.01); *G01N 2015/0046* (2013.01); *Y02A 50/25* (2018.01); *Y02B 30/78* (2013.01)

(58) Field of Classification Search
CPC .................................................. F24F 11/0017
See application file for complete search history.

(56) References Cited

U.S. PATENT DOCUMENTS

| | | | | |
|---|---|---|---|---|
| 6,525,334 B1 * | 2/2003 | Brackett | ............ | G01N 15/0656 250/222.2 |
| 9,791,361 B2 * | 10/2017 | Niemela | ............ | G01N 15/0656 |

(Continued)

FOREIGN PATENT DOCUMENTS

KR 10-2006-0112486 1/2006

*Primary Examiner* — Clayton E Laballe
*Assistant Examiner* — Dennis Hancock
(74) *Attorney, Agent, or Firm* — Staas & Halsey LLP

(57) ABSTRACT

An air conditioner includes a cabinet, a particle sensing unit coupled to the cabinet and configured to measure a particle concentration of an outside, and an inlet provided at the cabinet and configured to communicate with the outside so that particles flow into the particle sensing unit, and the particle sensing unit includes a first particle sensor configured to sense particles flowing in through the inlet, and a second particle sensor coupled to form a connection path in which particles move between the first particle sensor and the second particle sensor to sense the particles passing through the first particle sensor. The air conditioner allows the sensing of fine particles and ultrafine particles due to a plurality of particle sensors.

16 Claims, 11 Drawing Sheets

(56) References Cited

U.S. PATENT DOCUMENTS

2006/0150754 A1\* 7/2006 Burtscher ................. B03C 3/08
                                                            73/865.5
2011/0216317 A1\* 9/2011 Marra .................. G01N 1/2202
                                                            356/335

\* cited by examiner

AIR CONDITIONER

CROSS-REFERENCE TO RELATED APPLICATIONS

This application claims the priority benefit of Korean Patent Application No. 10-2015-0024055, filed on Feb. 17, 2015 in the Korean Intellectual Property Office, the disclosure of which is incorporated herein by reference.

BACKGROUND

1. Field

The following description relates to an air conditioner, and more particularly, to an air conditioner which includes a particle sensor configured to measure a particle concentration.

2. Description of the Related Art

Generally, an air conditioner is a device which controls temperature, humidity, air flow, a distribution and the like, by using a refrigeration cycle, and simultaneously removes particles and the like in air.

Recent air conditioners have an ability to clean air, by measuring a contamination degree of an interior to clean air, providing information on the air contamination degree of the interior to users, and may automatically control an operation state of an air conditioner according to the air contamination degree of the interior. Recently, the need to measure fine particles having a diameter of 10 μm or less and ultrafine particles having a diameter of 2.5 μm or less has been increased because of a changing environment.

Even though a conventional air conditioner may include a particle sensor, the particle sensor cannot sense fine particles or ultrafine particles which have been generated recently.

In addition, an additional filter is installed at an inlet in which a sensor is installed to prevent the influx of large-sized foreign material into an air conditioner. In this case, the manufacturing of an air conditioner is complex and the aesthetic quality thereof is decreased.

SUMMARY

Therefore, it is an aspect of the present disclosure to provide an air conditioner which includes particle sensors configured to sense particles having different sizes.

Additional aspects of the disclosure will be set forth in part in the description which follows and, in part, will be obvious from the description, or may be learned by practice of the disclosure.

In accordance with an aspect of the present disclosure, an air conditioner includes a cabinet, a particle sensing unit coupled to the cabinet and configured to measure a particle concentration, and an inlet provided at the cabinet and configured to communicate with the outside so that particles flow into the particle sensing unit, and the particle sensing unit includes a first particle sensor configured to sense particles flowing in through the inlet, and a second particle sensor coupled to form a connection path in which particles move between the first particle sensor and the second particle sensor to sense the particles passing through the first particle sensor.

The first particle sensor and the second particle sensor may be serially disposed.

The first particle sensor may be coupled to an upper side of the second particle sensor.

The first particle sensor may sense larger-sized particles than the second particle sensor.

The first particle sensor may sense smaller-sized particles than the second particle sensor.

Particles may move from the inlet through a communication hole provided at the first particle sensor to an inside of the first particle sensor, and a minimum height from a bottom thereof to the inlet may be different from a minimum height from the bottom to the communication hole of the first particle sensor.

The inlet may be provided at a bent portion configured to extend downward from a surface of the cabinet.

The particle sensing unit may further include a casing including a first accommodation portion accommodating the first particle sensor and a second accommodation portion accommodating the second particle sensor, and coupled to an inside of the cabinet.

The connection path may be provided at an inside of the casing and configured to slope in a direction of the second particle sensor to guide the movement of the particles.

The casing may be formed of an elastic material.

The particle sensing unit may further include a blower fan to suction particles, and the blower fan may be coupled to at least one of the first particle sensor and the second particle sensor.

The air conditioner may further include at least one sealing member coupled between the inlet and the particle sensing unit to prevent a gap from forming between the inlet and the particle sensing unit.

In accordance with an aspect of the present disclosure, an air conditioner includes cabinet, a particle sensing unit coupled to the cabinet and including at least one particle sensor to measure a particle concentration of an outside; an inlet provided to communicate with the outside so that particles flow into the particle sensing unit from an outside of the cabinet, and a communication hole provided in at least a part of the particle sensing unit, communicating with the inlet, and in which particles move from the inlet, and a minimum height from the inlet to a bottom thereof is different from a minimum height from the communication hole to the bottom thereof so that a part of particles flowing into the inlet flows into the particle sensing unit.

The inlet may be configured so that particles flow into the inlet, move upward, and flow into the communication hole.

The inlet may be provided at a bent portion configured to extend downward from a surface of the cabinet.

The particle sensing unit may include a first particle sensor configured to sense particles flowing in through the inlet, and a second particle sensor serially disposed with the first particle sensor to sense the particles which pass through the first particle sensor.

The particle sensing unit may further include a casing including a first accommodation portion accommodating the first particle sensor and a second accommodation portion accommodating the second particle sensor.

The particle sensing unit may further include a blower fan to enable particles to flow into the inlet and move to an inside of the particle sensing unit, and the blower fan may be coupled to a lower side of the particle sensor.

In accordance with an aspect of the present disclosure, an air conditioner includes a cabinet, at least one particle sensor coupled to the cabinet and configured to sense particles flowing into the cabinet, and a blower fan coupled to at least a part of the particle sensor and enabling particles to flow into the particle sensor from an outside of the cabinet, and a first path in which particles move due to an operation of the blower fan and a second path branched from the first path are included, and particles move through the first path and the second path.

The particle sensor may include a first particle sensor configured to sense particles flowing in through the first path, and a second particle sensor configured to sense particles flowing in through the second path.

The first particle sensor may be coupled to an upper side of the second particle sensor, and the blower fan is coupled to a lower side of the second particle sensor to move particles downward.

The air conditioner may further include a casing configured to accommodate the first particle sensor and the second particle sensor, and a connection path configured to form the first path in which particles move from the first particle sensor to the second particle sensor may be formed at an inside of the casing.

The particle sensor may include a communication hole communicating with the inlet, and a minimum height from the inlet to a bottom thereof may be different from a minimum height from the communication hole to the bottom thereof so that a part of particles flowing into the inlet flows into the particle sensing unit.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
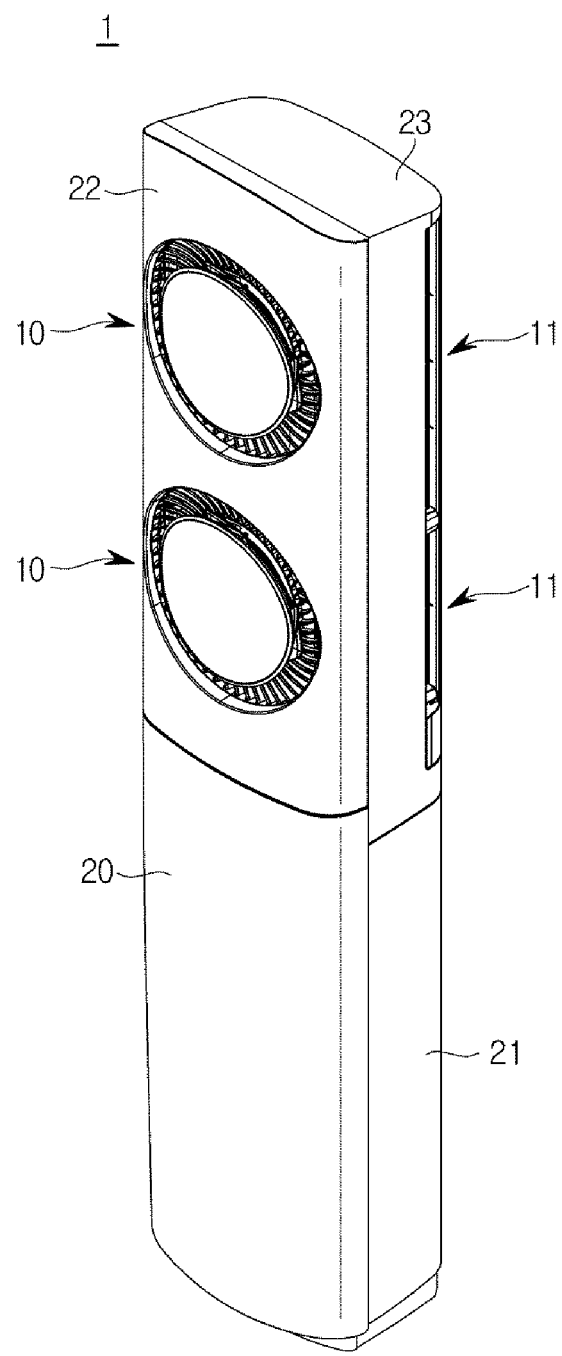
FIG. 1 is a perspective view illustrating an air conditioner according to an embodiment of the present disclosure.

Reference will now be made in detail to the embodiments of the present disclosure, examples of which are illustrated in the accompanying drawings, wherein like reference numerals refer to like elements throughout.

Figure 2:
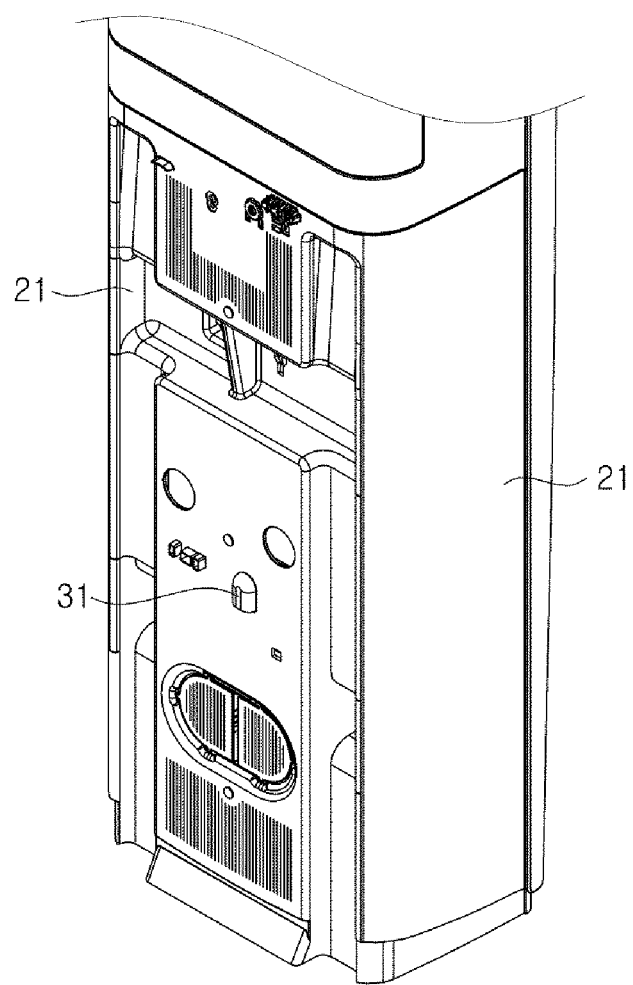
FIG. 2 is a view illustrating a back side of an air conditioner according to an embodiment of the present disclosure.
Figure 3:
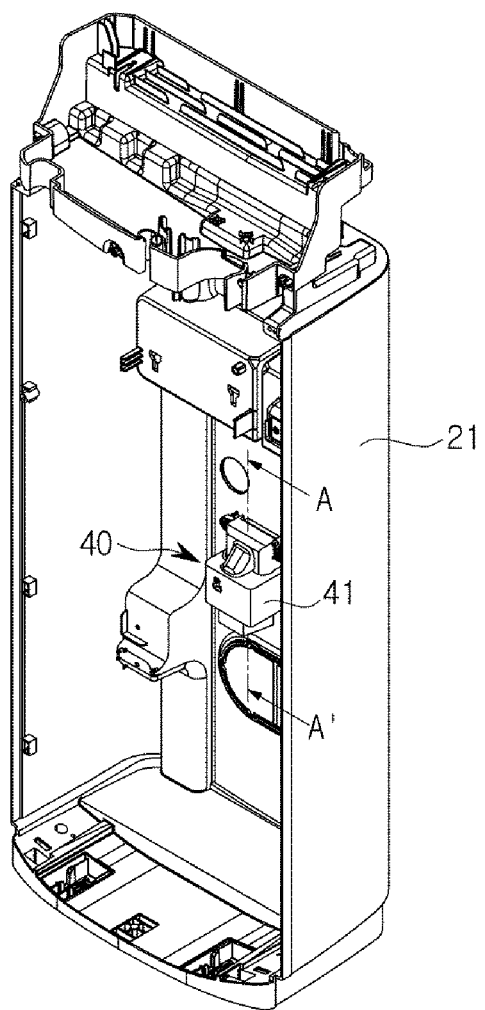
FIG. 3 is a view illustrating a state in which a front panel of an air conditioner according to an embodiment of the present disclosure is separated therefrom and a particle sensing unit is installed in a cabinet.

FIG. 1 is a perspective view illustrating an air conditioner according to an embodiment of the present disclosure, FIG. 2 is a view illustrating a back side of an air conditioner according to an embodiment of the present disclosure, and FIG. 3 is a view illustrating a state in which a front panel of an air conditioner according to an embodiment of the present disclosure is separated therefrom and a particle sensing unit is installed in a cabinet.

As illustrated in FIG. 1, a cabinet of an air conditioner 1 may include front panels 20 and 22 having at least one opening and back panels 21 and 23 disposed at a rear side of the front panels 20 and 22. The front panels 20 and 22 may include an upper front panel 22 having at least one discharge portion 10 and a lower front panel 20 having a space in which a refrigerant pipe (not shown) extends in an inside thereof. The back panels 21 and 23 may also include an upper back panel 23 and a lower back panel 21. The back panels 21 and 23 may have at least one intake 11. According to an embodiment of the present disclosure, the upper back panel 23 may include at least one intake 11.

An inside of the cabinet may include at least one heat exchanger (not shown) in which the heat exchange of air suctioned through the at least one intake 11 is performed, and at least one fan (not shown) disposed to be capable of rotating between the heat exchanger (not shown) and the discharge portion 10. The fan (not shown) may forcibly circulate air of which heat is exchanged at the heat exchanger (not shown) to be discharged through the discharge portion 10.

Air is suctioned through the intake 11, whose heat is exchanged at the heat exchanger (not shown), and the air is discharged through the discharge portion 10.

As illustrated in FIGS. 2 and 3, a particle sensing unit 40 may be installed in the cabinet so that particles flowing into an inlet 30 flow thereinto. Particularly, even though the particle sensing unit 40 may be installed at the back panels 21 and 23, it is not intended to be limited thereto. According to an embodiment of the present disclosure, the particle sensing unit 40 may be installed at the lower back panel 21. Accordingly, the inlet 30, configured to communicate with an outside, or exterior, of the air conditioner, may be provided at the lower back panel 21 so that particles flow into the particle sensing unit.

The inlet 30 may be integrally provided with the cabinet. According to an embodiment of the present disclosure, the inlet 30 may be provided at a bent portion 31 configured to extend downward from a surface of the lower back panel 21 of the cabinet. The bent portion 31 may be provided to protrude to the surface of the lower back panel 21. The inlet 30 may be formed at a lower side of the bent portion 31. Accordingly, particles may move in an upper direction from the inlet 30 and flow into the particle sensing unit 40. Thus, heavy foreign material, such as textile particles or pet fur, does not flow into the inlet 30, and falls downward due to gravity, and material flowing into the inlet 30 may be filtered according to the sizes thereof. This will be described below.

Figure 4:
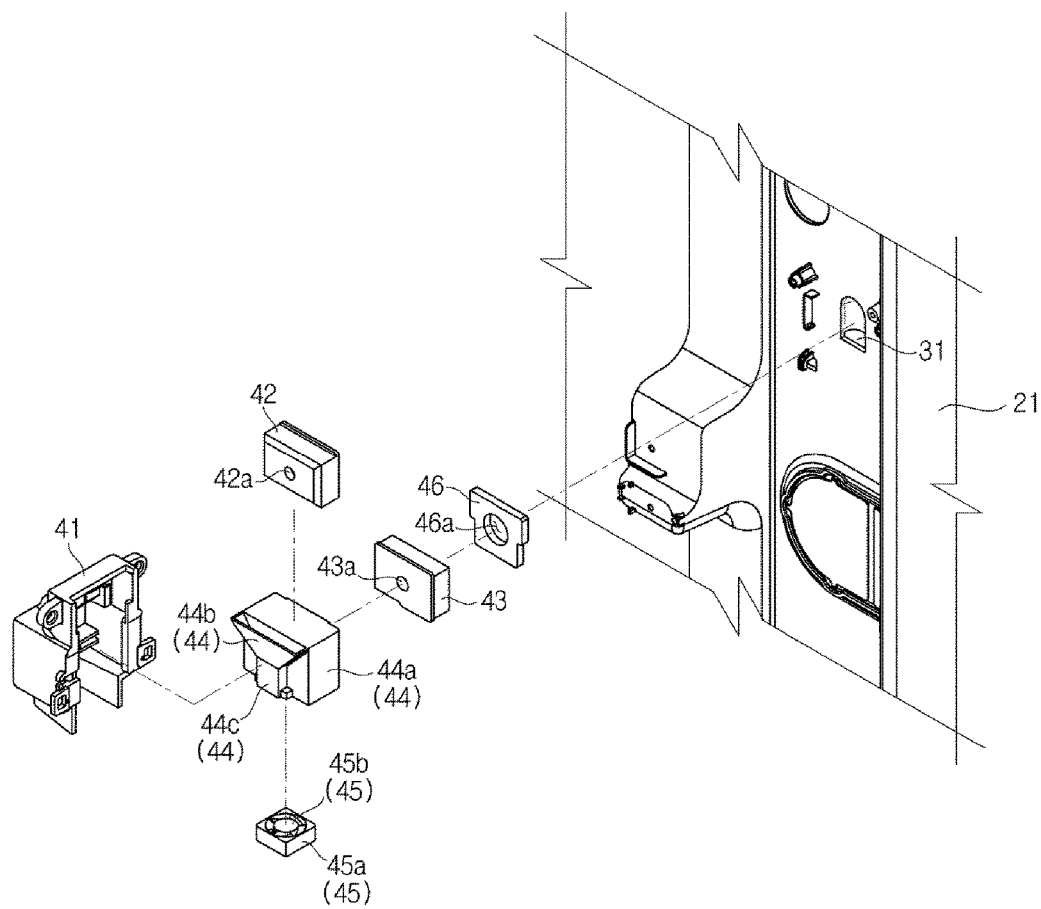
FIG. 4 is an exploded view illustrating a separated particle sensing unit of an air conditioner according to an embodiment of the present disclosure.
Figure 5:
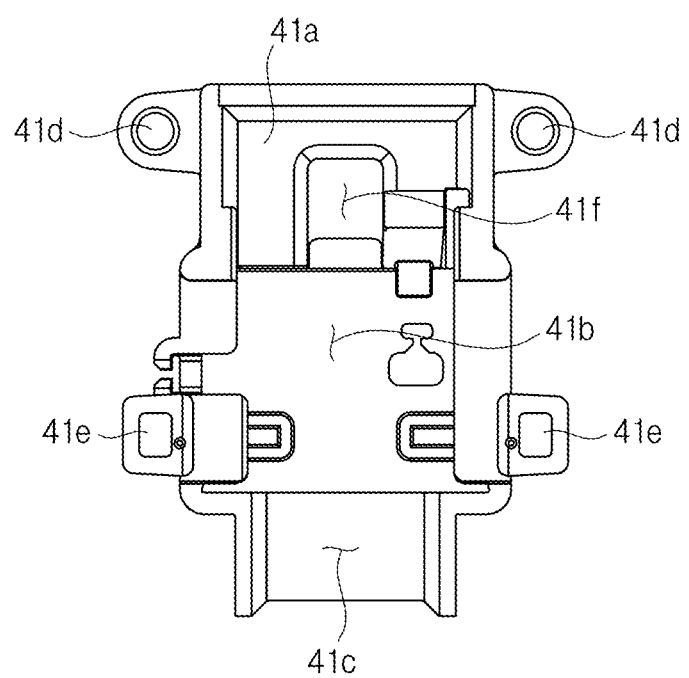
FIG. 5 is a view illustrating a casing of a particle sensing unit of an air conditioner according to an embodiment of the present disclosure.

FIG. 4 is an exploded view illustrating a separated particle sensing unit of an air conditioner according to an embodiment of the present disclosure, and FIG. 5 is a view illustrating a casing of a particle sensing unit of an air conditioner according to an embodiment of the present disclosure.

As illustrated in FIG. 4, the particle sensing unit 40 includes a first particle sensor 42 and a second particle sensor 43. The first particle sensor 42 and the second particle sensor 43 are sensors configured to respectively sense fine particles and ultrafine particles. According to an embodiment of the present disclosure, even though the first particle sensor 42 may sense fine particles having a diameter less than or equal to 10 μm and the second particle sensor 43 may sense ultrafine particles having a diameter less than or equal to 2.5 μm, the disclosure is not limited thereto, and the vice versa may also be allowed. That is, the first particle sensor may sense ultrafine particles, and the second particle sensor may sense fine particles.

According to an embodiment of the present disclosure, the second particle sensor 43 may be accommodated in a second particle sensor housing 44. A main body 44a of the second particle sensor housing 44 may include guide ducts 44b and 44c configured to guide particles which pass through the first particle sensor 42 to a sensing portion (not shown) of the second particle sensor 43. The guide ducts 44b and 44c may include a first guide duct 44b and a second guide duct 44c. The first guide duct 44b may be provided to be more adjacent to the first particle sensor 42 than the second guide duct 44c. The first guide duct 44b may be provided in a shape in which a diameter decreases from top to bottom. This is to guide particles which pass through the first particle sensor 42 to the second particle sensor 43 because the first particle sensor 42 is located above the second particle sensor 43. At least a part of the second guide duct 44c branches from a flow path in which particles move, thus, a portion of the particles passes through the second guide duct 44c, and the other part thereof moves to the sensing portion (not shown) of the second particle sensor 43. This will be described below.

According to an embodiment of the present disclosure, the particle sensing unit 40 may further include a blower fan 45b configured to suction particles. The blower fan 45b is accommodated in a fan housing 45a and configures a blower fan unit 45. The blower fan unit 45 is coupled to at least a part of the second particle sensor 43, but it is not limited thereto, and the blower fan unit 45 is capable of being coupled to the first particle sensor 42. The blower fan unit 45 may be coupled to a lower side of the second particle sensor 43, enable particles to flow in through the inlet 30 and move downward, and enable the first particle sensor 42 and the second particle sensor 43 to sense the particles.

At least one sealing member 46 may be coupled between the inlet 30 and the particle sensing unit 40. The sealing member 46 may prevent a gap from being generated between the inlet 30 and the particle sensing unit 40. In addition, the sealing member 46 buffers noise or vibration generated from the particle sensing unit 40 to prevent the noise or vibration from being transmitted to an outside thereof. The sealing member 46 may be tightly coupled to an inner side of the lower back panel 21 of the cabinet to prevent a gap from being generated between the inlet 30 and the particle sensing unit 40. A hole 46a provided in the sealing member 46 may be provided for communication with the inlet 30. Thus, particles flowing into the inlet 30 pass through the hole 46a of the sealing member 46 and move to a communication hole 42a of the first particle sensor 42.

According to an embodiment of the present disclosure, the first particle sensor 42 and the second particle sensor 43 are accommodated in a casing 41. The casing 41 may be formed to be coupled to the cabinet. The casing 41 may include a first accommodation portion 41a accommodating the first particle sensor 42 and a second accommodation portion 41b accommodating the second particle sensor 43. In addition, the casing 41 may include a third accommodation portion 41c accommodating the blower fan unit 45. The first accommodation portion 41a and the second accommodation portion 41b of the casing 41 may be respectively provided to correspond to shapes of the first particle sensor 42 and the second particle sensor 43.

The casing 41 may include at least one of fastening portions 41d and 41e for coupling to the lower back panel 21 of the cabinet. According to an embodiment of the present disclosure, two first fastening portions 41d may be provided at an upper portion of the casing 41, and two second fastening portions 41e may be provided at a lower portion thereof. The first fastening portion 41d may be coupled to the lower back panel 21 by an additional fastening member (not shown). The second fastening portion 41e may be coupled to the lower back panel 21 by a hook-fastening method.

A connection path 41f in which particles move from the first particle sensor 42 to the second particle sensor 43 may be formed in the casing 41. The connection path 41f may be provided obliquely in the second particle sensor 43 direction. That is, the connection path 41f may be formed to slope downward. This is to guide particles which pass through the first particle sensor 42 to flow into the second particle sensor 43.

The casing 41 may be formed of an elastic material. It is to absorb noise and vibration generated by the particle sensors 42 and 43. In addition, because the casing 41 is formed of an elastic material, the particle sensors 42 and 43 and the blower fan 45b may be flexibly accommodated in the casing 41. More specifically, the casing 41 may be formed of a rubber. Particularly, the casing 41 may be formed of acrylonitrile-butadiene rubber (NBR).

Figure 6:
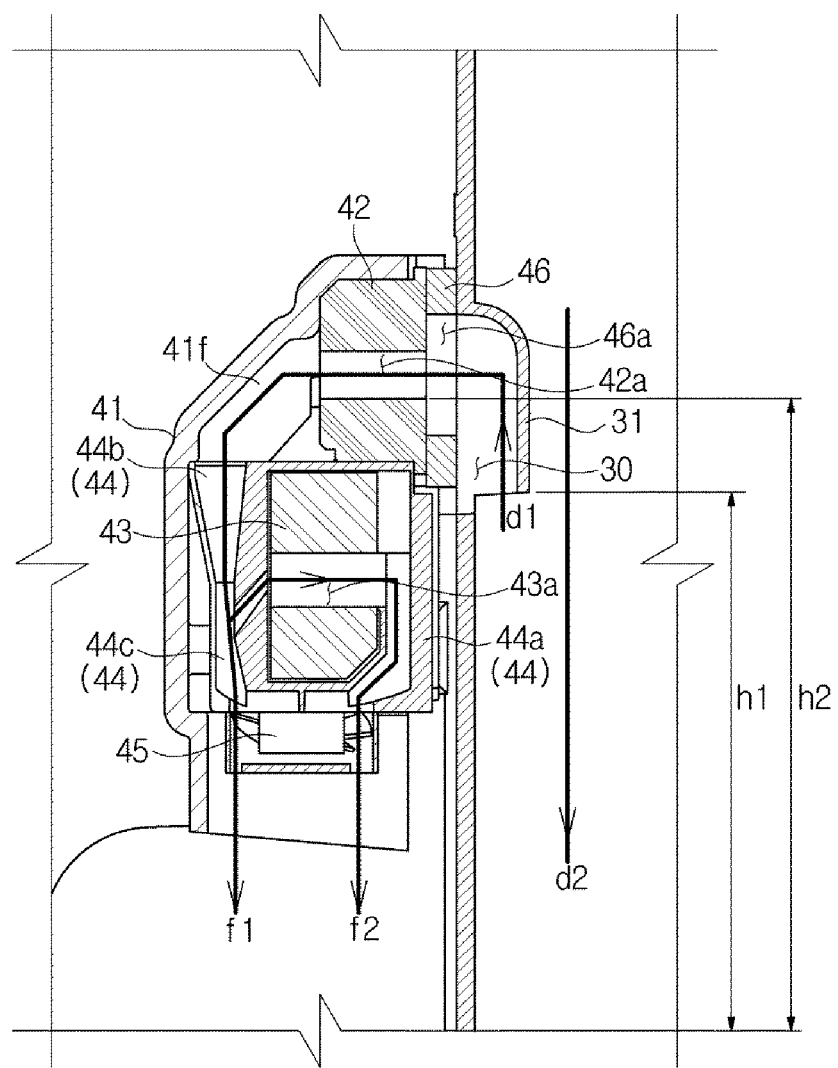
FIG. 6 is a cross sectional view taken along line A-A' of the FIG. 3.

FIG. 6 is a cross sectional view taken along line A-A' of the FIG. 3.

As illustrated in FIG. 6, the first particle sensor 42 senses particles flowing in through the inlet 30, and is coupled to the second particle sensor 43 to form the connection path 41f in which the particles move between the first particle sensor 42 and the second particle sensor 43 so that the second particle sensor 43 senses a part of the particles which pass through the first particle sensor 42. The first particle sensor 42 and the second particle sensor 43 may be coupled to each other in such a manner that at least a part of each is in contact with at least a part of the other. The first particle sensor 42 and the second particle sensor 43 may be serially disposed. In the view, even though the first particle sensor 42 is coupled to an upper side of the second particle sensor 43, the disclosure is not limited thereto, and the second particle sensor 43 is capable of being coupled to a side surface of the first particle sensor 42. Because the first particle sensor 42 and the second particle sensor 43 are serially disposed, even though there is one inlet 30 into which particles flow from an outside, a measurement of a contamination degree is allowed because particles move from the first particle sensor 42 to the second particle sensor 43. According to an embodiment of the present disclosure, the structure of the particle sensing unit 40 may be simplified because a plurality of inlets are not needed.

According to an embodiment of the present disclosure, the inlet 30 and the communication hole 42a may not be provided horizontally. That is, the inlet 30 and the communication hole 42a may not be formed at the same height. More specifically, the minimum height h1 of the inlet 30 from the bottom thereof is different from the minimum height h2 of the communication hole 42a of the first particle sensor 42 from the bottom. Accordingly, as shown in the drawing, the inlet 30 may be provided at a lower height than the communication hole 42a. That is, the minimum height h1 of the inlet 30 from the bottom may be smaller than the minimum height h2 of the communication hole 42a of the first particle sensor 42 from the bottom. However, the disclosure is not limited thereto, and the inlet may be provided at a higher position than the communication hole.

According to an embodiment of the present disclosure, when the inlet 30 is provided at a lower position than the communication hole 42a, particles need to move upward to flow into the inlet 30. Thus, large-sized particles do not flow into the inlet 30 and fall due to gravity (Refer to d2 of FIG. 6). Because fine particles and ultrafine particles being small-sized are not comparatively influenced by gravity, the fine particles and ultrafine particles move upward due to a suction force of the blower fan 45b and flow into the inlet 30 (Refer to d1 of FIG. 6). Thus, a structure of the inlet 30 and the communication hole 42a is capable of a first filtering of particles without an additional member.

Next, the movement of particles flowing into the particle sensing unit 40 will be described below.

Particles flowing into the inlet 30 due to an operation of the blower fan 45b pass through the particle sensing unit 40 and move downward. The path in which particles move may include a first path f1 and a second path f2 branched from the first path f1.

The first path f1 is a path in which particles move to the second particle sensor 43 through the communication hole 42a and the connection path 41f. A part of particles which move to the guide ducts 44b and 44c adjacent to the second particle sensor 43 moves to the first path f1 due to the operation of the blower fan 45b, and the remaining part including small-sized ultrafine particles flows into the communication hole 43a of the second particle sensor 43 due to the second path f2 branched from the first path f1. The particles which flow into the second path f2 are sensed by the second particle sensor 43, pass through the second particle sensor 43 due to the operation of the blower fan 45b, pass through the blower fan unit 45, and fall.

The particles flowing in through the first path f1 are sensed by the first particle sensor 42, the particles flowing from the first path f1 into the second path f2 are sensed by the second particle sensor 43.

According to an embodiment of the present disclosure, the air conditioner is capable of measuring the concentration of fine particles and ultrafine particles in air by particles flowing into one inlet 30. In addition, the degree of air contamination may be effectively measured because of the movement of particles due to the blower fan 45b.

Figure 7:
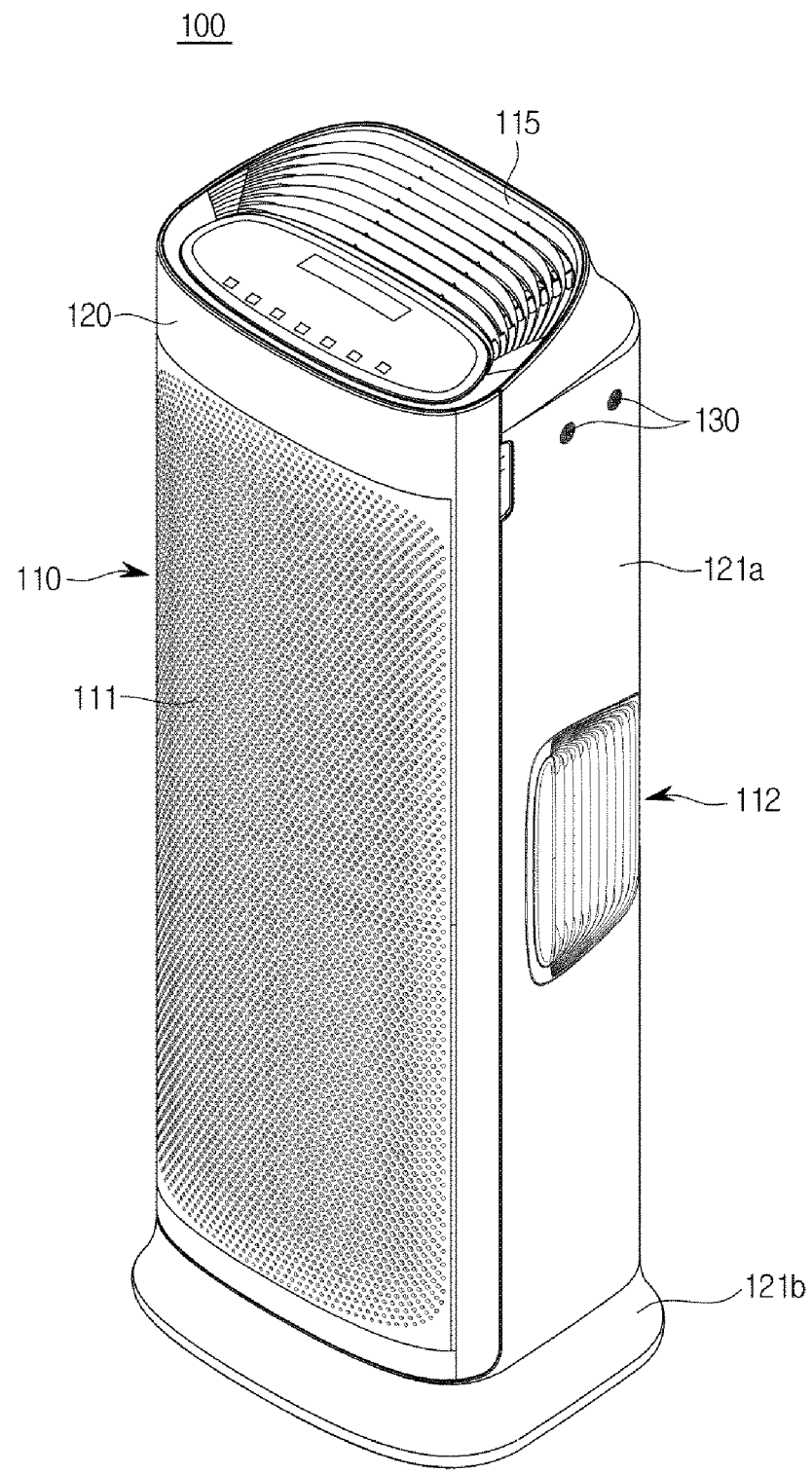
FIG. 7 is a perspective view illustrating an air conditioner according to an embodiment of the present disclosure.
Figure 8:
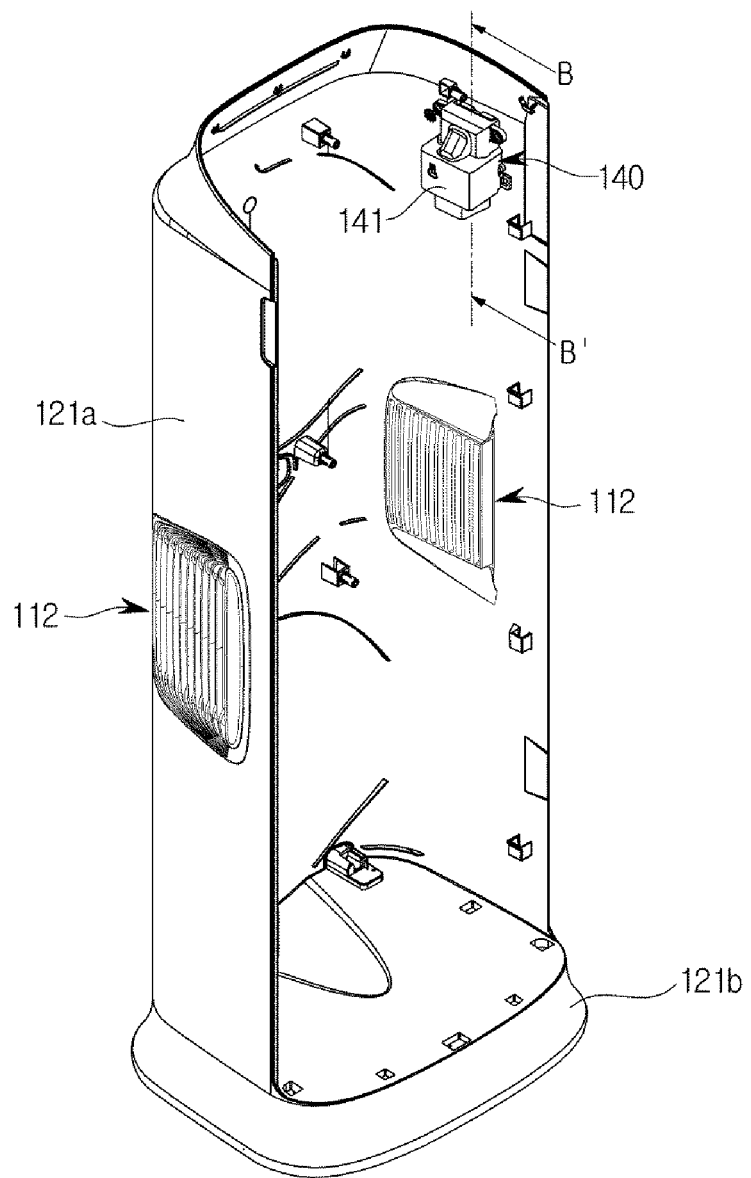
FIG. 8 is a view illustrating a state in which a front panel of an air conditioner according to an embodiment of the present disclosure is separated therefrom and a particle sensing unit is installed in a cabinet.

FIG. 7 is a perspective view illustrating an air conditioner according to an embodiment of the present disclosure, and FIG. 8 is a view illustrating a state in which a front panel of an air conditioner according to an embodiment of the present disclosure is separated therefrom and a particle sensing unit is installed in a cabinet.

As illustrated in FIG. 7, an air conditioner 100 includes a cabinet which forms the appearance thereof. The cabinet may include a front panel 120 configured to form a front side of the air conditioner 100 and a back panel 121a configured to be coupled to the front panel 120 and form a back side of the air conditioner 100. In addition, the cabinet may include a bottom panel 121b provided to form a bottom.

An intake 110 is formed at the front panel 120 so that air flows in from an outside of the air conditioner. The intake 110 may be formed by including a plurality of intake holes 111 uniformly disposed in most of an entire surface of the front panel 120. The intake 110 of the front panel 120 may be formed so that outside air flows inward from a front side of the cabinet.

Air which flows into an inside of the cabinet through the intake 110 may be discharged to an outside through discharge portions 112 and 115. The discharge portions 112 and 115 may include a first discharge portion 112 and a second discharge portion 115. The first discharge portion 112 may be disposed on both sides of the back panel 121a of the cabinet. The second discharge portion 115 may be disposed on an upper side of the cabinet.

Even though an inlet 130 may be disposed on a side of the back panel 121a, the disclosure is not limited thereto. According to an embodiment of the present disclosure, the inlet 130 may be provided as a hole at the back panel 121a. A particle sensing unit 140 may be coupled to an inside of a side of the back panel 121a to sense particles which flow into the inlet 130. A coupling relation of the inlet 130 and the particle sensing unit 140 will be described below.

Figure 9:
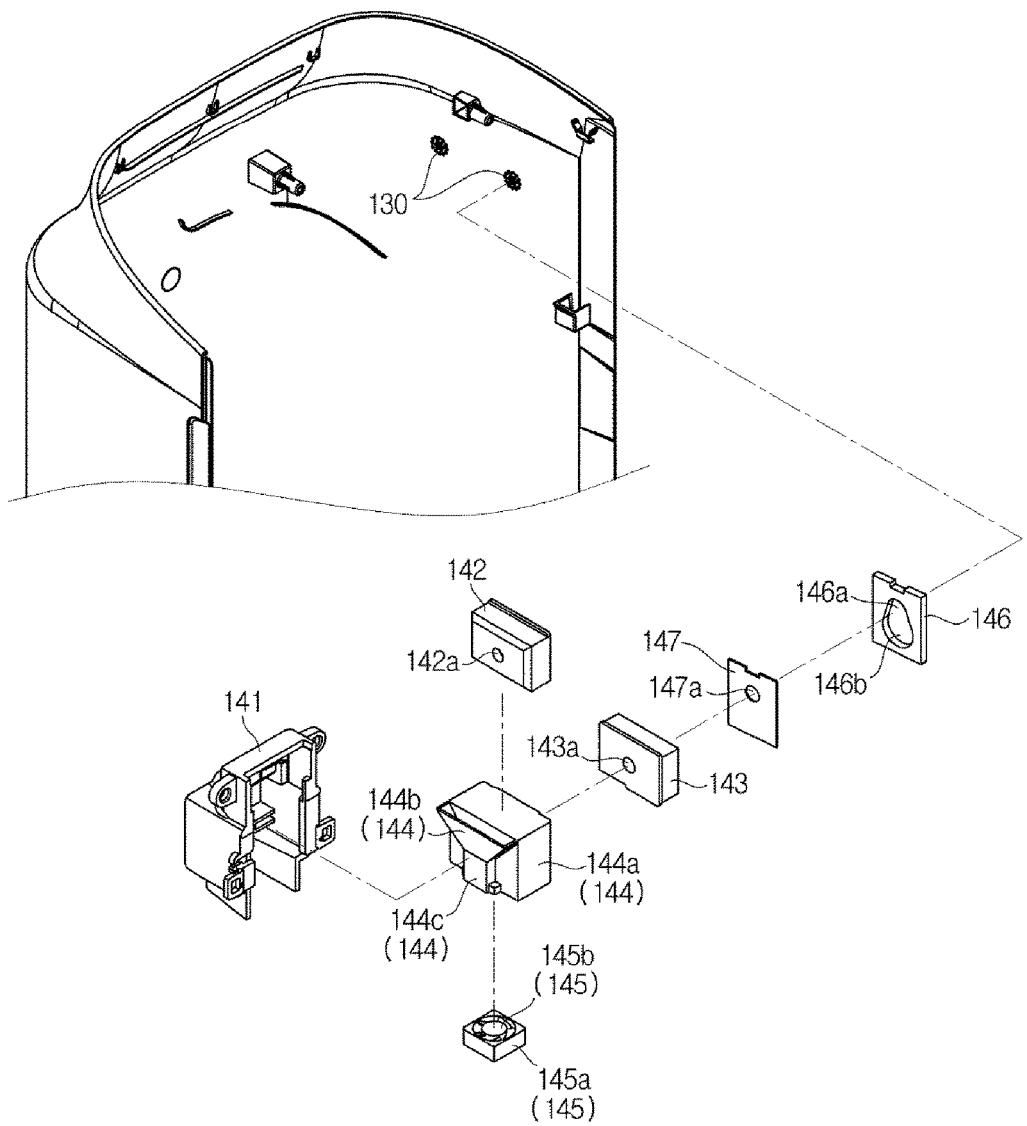
FIG. 9 is an exploded view illustrating a separated particle sensing unit of an air conditioner according to an embodiment of the present disclosure.
Figure 10:
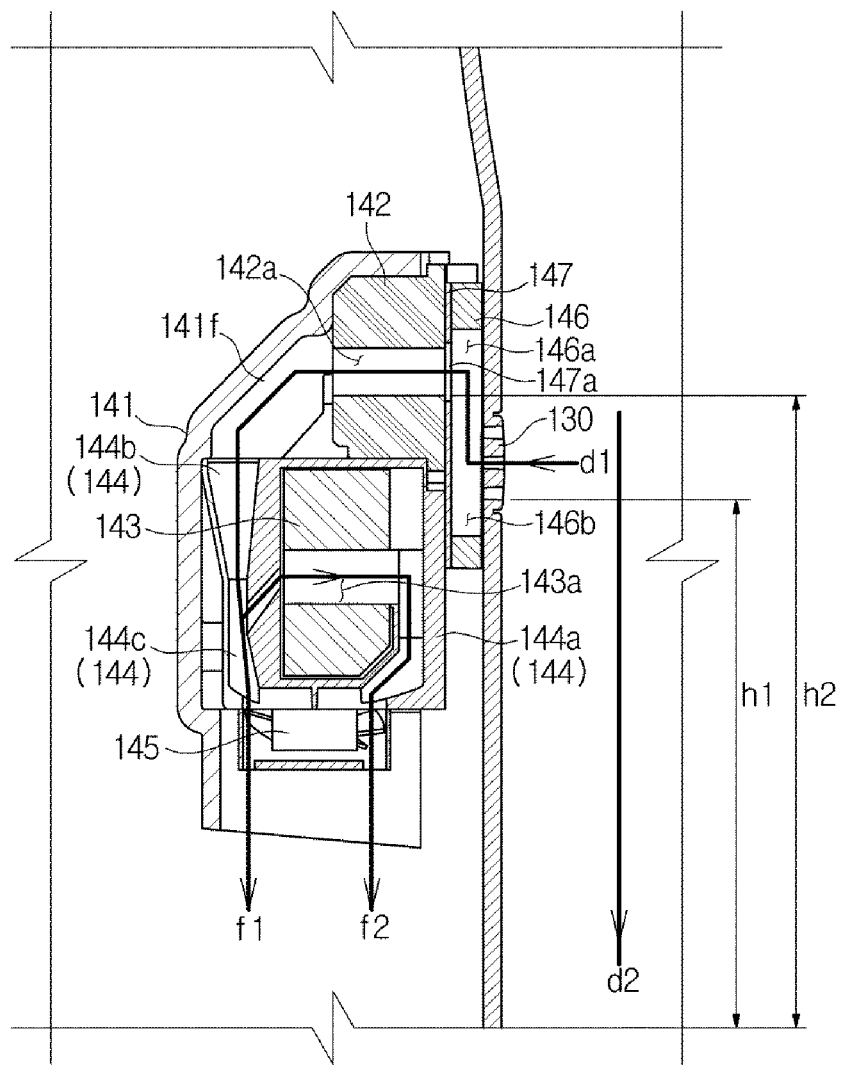
FIG. 10 is a cross sectional view taken along line B-B' of the FIG. 8.

FIG. 9 is an exploded view illustrating a separated particle sensing unit of an air conditioner according to an embodiment of the present disclosure, and FIG. 10 is a cross sectional view taken along line B-B' of FIG. 8.

The particle sensing unit 140 may include a casing 141, a connection path 141f, and a first particle sensor 142 and a second particle sensor 143 accommodated in the casing 141. The second particle sensor 143 includes a second particle sensor housing 144, and a first guide duct 144b and a second guide duct 144c may be coupled to a main body 144a of the second particle sensor housing 144. A blower fan unit 145 may be coupled to the second particle sensor 143. The blower fan unit 145 may include a fan housing 145a and a blower fan 145b.

According to an embodiment of the present disclosure, at least one of sealing members 146 and 147 may be coupled between the inlet 130 and the particle sensing unit 140. As illustrated in FIG. 9, a first sealing member 146 and a second sealing member 147 may be coupled between the inlet 130 and the particle sensing unit 140. A first sealing member 146 is coupled to an inside of the back panel 121a of the cabinet to communicate with the inlet 130, the second sealing member 147 may be coupled to the first sealing member 146. First holes 146a and 146b configured to communicate with the inlet 130 may be provided at the first sealing member 146, and a second hole 147a configured to cause the first holes 146a and 146b of the first sealing member 146 to communicate with a communication hole 142a of the first particle sensor 142 may be provided at the second sealing member 147. Particles flow through the inlet 130, pass through the first holes 146a and 146b and the second hole 147a, and flow into the particle sensing unit 140 through the communication hole 143a.

The first holes 146a and 146b may include a first area 146a and a second area 146b. The first area 146a is an area corresponding to the second hole 147a. The second area 146b is extended from the first area 146a, and may be provided at a lower position than the second hole 147a. That is, the diameter of the first hole 146a may be greater than that of the second hole 146b. According to an embodiment of the present disclosure, because the inlet 130 is provided at a lower position than the communication hole 142a, the first holes 146a and 146b are formed to include the first area 146a and the second area 146b to guide particles flowing from the inlet 130 to the communication hole 142a located above the inlet 130. Particles flowing into the inlet 130 and flowing into the first holes 146a and 146b may move upward due to a suction force of the blower fan 145b, pass through the second hole 147a, and flow into the communication hole 142a of the first particle sensor 142.

According to an embodiment of the present disclosure, the minimum distance h1 between the inlet 130 and the floor may be smaller than the minimum distance h2 between the communication hole 142a and the floor. Thus, large-sized particles are not capable of flowing into the inlet 130 and fall due to gravity (Refer to d2 of FIG. 10). On the contrary, small-sized particles such as fine particles and ultrafine particles flow into the inlet 130 (Refer to d1 of FIG. 10), and may be capable of passing through the first path f1 and the second path f2.

According to an embodiment of the present disclosure as illustrated in FIGS. 7 to 10, because the inlet 130 is provided in a hole shape formed at the cabinet and the communication hole 142a is located above the inlet 130, large-sized particles are filtered and there simultaneously is an advantage in which the appearance of the air conditioner 100 is elegant.

Figure 11:
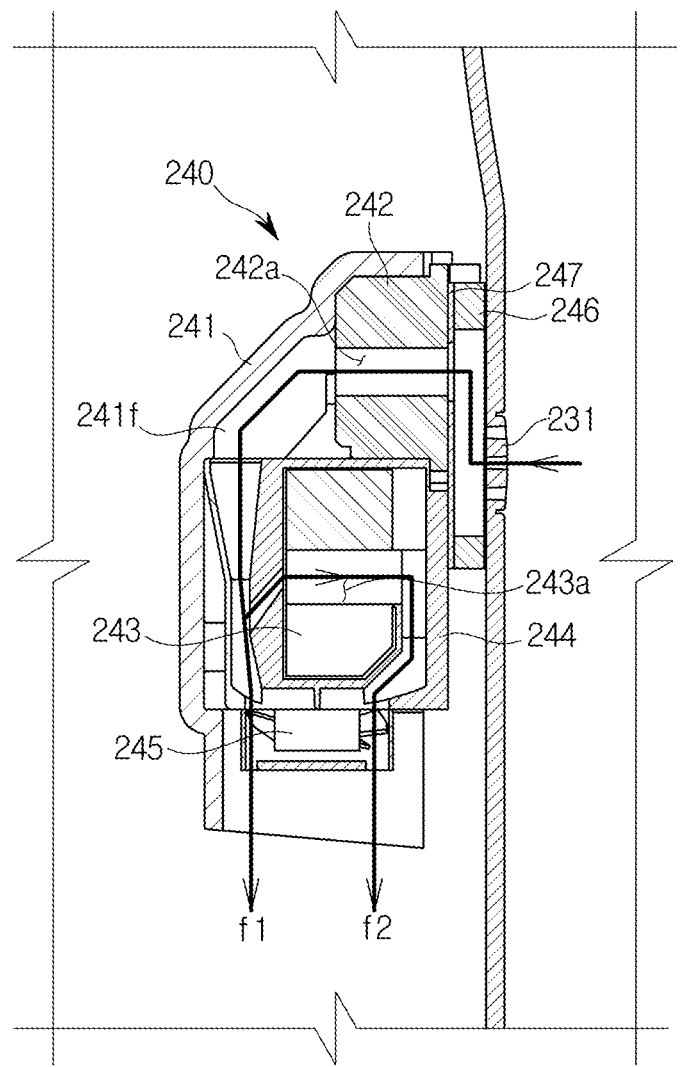
FIG. 11 is a view illustrating a state in which a front panel of an air conditioner according to an embodiment of the present disclosure is separated therefrom and a particle sensing unit is installed in a cabinet.

FIG. 11 is a view illustrating a state in which a front panel of an air conditioner according to an embodiment of the present disclosure is separated therefrom and a particle sensing unit is installed in a cabinet.

As illustrated in FIG. 11, an air conditioner may include an inlet 231 and a particle sensing unit 240. The particle sensing unit 240 may include a casing 241, and a first particle sensor 242 and a second particle sensor 243 accommodated in the casing 241. In addition, a first sealing member 246 and a second sealing member 247 may be provided between the inlet 231 and the particle sensing unit 240. According to an embodiment of the present disclosure as illustrated in FIG. 11, the first particle sensor 242 may sense fine particles, and the second particle sensor 243 may sense ultrafine particles. A connection path 241f which is a path configured to move particles from the first particle sensor 242 to the second particle sensor 243 may be provided at an inside of the casing 241. The second particle sensor 243 may include a second particle sensor housing 244 and a communication path 243a. A blower fan unit 245 may be coupled to the second particle sensor 243.

According to an embodiment of the present disclosure as illustrated in FIG. 11, particles flowing in through the inlet 231 pass through a first sealing member 246 and a second sealing member 247, and flow into the particle sensing unit 240 through a communication hole 242a. In addition, particles move along a first path f1 and a second path f2.

The air conditioner according to an embodiment of the present disclosure can sense fine particles and ultrafine particles using a plurality of particle sensors.

In addition, the appearance of an air conditioner may not suffer and an inflow of large-sized particles can be simultaneously prevented because of the coupled-structure of a plurality of particle sensors and inlets.

In addition, the change in indoor air can be quickly sensed compared to a conventional air conditioner because a blower fan installed at a particle sensor suctions outside air and particles flow into an inside of a cabinet.

In the above, specific embodiments of the present disclosure are illustrated and described. However, the present disclosure is not limited to the embodiments described above, and it will be understood by those skilled in the art that various modifications and alternations may be made without departing from the spirit and scope described in the appended claims.

What is claimed is:
1. An air conditioner comprising:
a cabinet;
a particle sensing unit coupled to an inside of the cabinet and configured to measure a particle concentration;
and an inlet provided at the cabinet and configured to communicate with the outside of the air conditioner so that particles flow into the particle sensing unit, wherein the particle sensing unit includes:
a first particle sensor configured to sense particles flowing through the first particle sensor from the inlet; and
a second particle sensor, coupled by a connection path to the first particle sensor, configured to sense the particles flowing through the second particle sensor and having passed through the first particle sensor,
wherein the inlet is configured to suction the air in an upward direction into the inlet and divert the suctioned air to flow into the first particle sensor in a second direction substantially perpendicular to the upward direction.

2. The air conditioner of claim 1, wherein the first particle sensor and the second particle sensor are serially disposed, and
wherein the first particle sensor is coupled to an upper side of the second particle sensor.

3. The air conditioner of claim 1, wherein the first particle sensor senses larger-sized particles than the second particle sensor.

4. The air conditioner of claim 1, wherein the first particle sensor senses smaller-sized particles than the second particle sensor.

5. The air conditioner of claim 1,
wherein the particles move from the inlet through a communication hole provided at the first particle sensor to an inside of the first particle sensor, and
wherein a minimum height from a bottom of the air conditioner to the inlet is different from a minimum height from the bottom of the air conditioner to the communication hole of the first particle sensor.

6. The air conditioner of claim 1, wherein the particle sensing unit further includes a casing including a first accommodation portion accommodating the first particle sensor and a second accommodation portion accommodating the second particle sensor, and coupled to an inside of the cabinet.

7. The air conditioner of claim 6, wherein the connection path is provided at an inside of the casing and configured to slope in a direction of the second particle sensor to guide the movement of the particles.

8. The air conditioner of claim 6, wherein the casing is formed of an elastic material.

9. The air conditioner of claim 1, wherein the particle sensing unit further includes a blower fan to suction particles, and the blower fan is coupled to at least one of the first particle sensor and the second particle sensor.

10. The air conditioner of claim 1, further comprising:
at least one sealing member coupled between the inlet and the particle sensing unit to prevent a gap from being formed between the inlet and the particle sensing unit.

11. An air conditioner comprising:
a cabinet;
a particle sensing unit coupled to the cabinet and including at least one particle sensor to measure a particle concentration;
an inlet provided to communicate directly with the outside of the cabinet and facing a downward direction so that particles flow through the inlet into the particle sensing unit from the outside of the cabinet; and a communication hole provided in the particle sensing unit and facing a direction substantially perpendicular to the downward direction, configured to communicate with the inlet, and in which the particles move from the inlet through an inside of the cabinet into the particle sensing unit, wherein a minimum height from the inlet to a bottom of the air conditioner is different from and less than a minimum height from the communication hole to the bottom of the air conditioner so that a first portion of the particles flowing into the inlet flows into the particle sensing unit and a second portion of the particles flowing into the inlet does not flow into the particle sensing unit due to gravity.

12. The air conditioner of claim 11, wherein the inlet is configured so the particles flow into the inlet, move in an upward direction, and flow into the communication hole in a direction substantially perpendicular to the upward direction.

13. The air conditioner of claim 12, wherein the inlet is provided at a bent portion configured to extend downward from a surface of the cabinet.

14. The air conditioner of claim 11, wherein the particle sensing unit includes a first particle sensor configured to sense the particles flowing in through the inlet, and a second particle sensor serially disposed with the first particle sensor to sense the particles which pass through the first particle sensor.

15. The air conditioner of claim 14, wherein the particle sensing unit further includes a casing including a first accommodation portion accommodating the first particle sensor and a second accommodation portion accommodating the second particle sensor.

16. The air conditioner of claim 11, wherein the particle sensing unit further includes a blower fan to enable the particles to flow into the inlet and move to an inside of the particle sensing unit, and the blower fan is coupled to a lower side of the particle sensor.

\* \* \* \* \*